(12) United States Patent
Kawano

(10) Patent No.: US 9,693,962 B2
(45) Date of Patent: Jul. 4, 2017

(54) DRY-COATED TABLET

(71) Applicant: Takeda Pharmaceutical Company Limited, Osaka-shi, Osaka (JP)

(72) Inventor: Tetsuya Kawano, Osaka (JP)

(73) Assignee: Takeda Pharmaceutical Limited, Osaka (JP)

(*) Notice: Subject to any disclaimer, the term of this patent is extended or adjusted under 35 U.S.C. 154(b) by 0 days.

(21) Appl. No.: 14/405,310

(22) PCT Filed: May 28, 2013

(86) PCT No.: PCT/JP2013/064795
§ 371 (c)(1),
(2) Date: Dec. 3, 2014

(87) PCT Pub. No.: WO2013/183497
PCT Pub. Date: Dec. 12, 2013

(65) Prior Publication Data
US 2015/0132379 A1 May 14, 2015

(30) Foreign Application Priority Data

Jun. 5, 2012 (JP) .................................. 2012-128336

(51) Int. Cl.
*A61K 9/20* (2006.01)
*A61K 31/4439* (2006.01)
(Continued)

(52) U.S. Cl.
CPC .......... *A61K 9/2072* (2013.01); *A61K 9/2013* (2013.01); *A61K 9/2027* (2013.01);
(Continued)

(58) Field of Classification Search
CPC ....... A61K 9/20; A61K 9/2027; A61K 9/2095
See application file for complete search history.

(56) References Cited

U.S. PATENT DOCUMENTS

| | | | |
|---|---|---|---|
| 3,146,169 A | 8/1964 | Stephenson et al. | |
| 6,406,738 B1* | 6/2002 | Hogan | A61J 3/005 427/128 |

(Continued)

FOREIGN PATENT DOCUMENTS

| | | |
|---|---|---|
| JP | 2000-302672 | 10/2000 |
| JP | 2001-072579 | 3/2001 |

(Continued)

OTHER PUBLICATIONS

Antiplatelet Agent Bayaspirin (Registered Mark) Tablet 100 mg(aspirin enteric tablet), 2008, 6 pages including a partial English translation.

(Continued)

*Primary Examiner* — Lakshmi Channavajjala
(74) *Attorney, Agent, or Firm* — Hamre, Schumann, Mueller & Larson, P.C.

(57) ABSTRACT

A dry-coated tablet 1 comprises an inner core 2 which contains an active component and an outer layer 3 which contains powdery solid components and coats the inner core 2. Openings 8c and 9c are formed in circular surfaces 2a and 2b respectively of the inner core 2, wherein each of the openings is larger than the average particle size of a component the average particle size of which is the smallest of the powdery solid components contained in the outer layer 3, and the inner surface 3a of the outer layer 3 penetrates in the openings 8c and 9c.

12 Claims, 13 Drawing Sheets

(51) Int. Cl.
*A61K 31/616* (2006.01)
*A61K 9/28* (2006.01)

(52) U.S. Cl.
CPC .......... *A61K 9/2054* (2013.01); *A61K 9/2059* (2013.01); *A61K 9/2077* (2013.01); *A61K 9/2086* (2013.01); *A61K 9/2095* (2013.01); *A61K 9/2846* (2013.01); *A61K 9/2866* (2013.01); *A61K 31/4439* (2013.01); *A61K 31/616* (2013.01)

(56) References Cited

U.S. PATENT DOCUMENTS

| | | | | |
|---|---|---|---|---|
| 8,545,887 | B2* | 10/2013 | Sowden | A23G 1/54 424/464 |
| 9,233,076 | B2* | 1/2016 | O'Donnell | A61K 9/2072 |
| 2003/0039691 | A1 | 2/2003 | Waterman | |
| 2003/0068367 | A1 | 4/2003 | Sowden et al. | |
| 2003/0143257 | A1 | 7/2003 | Fleshner-Barak et al. | |
| 2003/0143272 | A1* | 7/2003 | Waterman | A61K 9/0004 424/471 |
| 2013/0243859 | A1 | 9/2013 | Mima et al. | |
| 2014/0023708 | A1 | 1/2014 | Harada et al. | |

FOREIGN PATENT DOCUMENTS

| | | |
|---|---|---|
| JP | 2002-275053 | 9/2002 |
| JP | 2005-502625 | 1/2005 |
| JP | 2005-511515 | 4/2005 |
| WO | 2005/097041 | 10/2005 |
| WO | 2012/074110 | 6/2012 |
| WO | 2012/118180 | 9/2012 |
| WO | 2013/081177 | 6/2013 |

OTHER PUBLICATIONS

Extended European Search Report issued in counterpart European Patent Application Serial No. 13800510.3, Dec. 1, 2015, 6 pages.

* cited by examiner

DRY-COATED TABLET

The present invention relates to a dry-coated tablet.

BACKGROUND ART

There is a case where a dry-coated tablet comprising an inner core portion and a coating portion is used for the purpose of masking a bitter taste and separating components. For example, in Patent Literature 1, a dry-coated tablet comprising (a) at least one inner core portion comprising a heat-melting base containing a medicament as an active component and (b) a coating portion including the inner core portion is disclosed.

CITATION LIST

Patent Literature

Patent Literature 1: Japanese Patent Application Laid-Open No. 2001-72579

SUMMARY OF INVENTION

Technical Problem

There is a case where, in dry-coated tablets, the strength generally becomes lower compared to tablets which do not have a layered structure, and it is necessary to handle them with care at the point of manufacturing and packaging, in the course of distribution, or on taking out from the package before ingestion, not to cause breaking, chipping and the like.

The present invention aims to provide a dry-coated tablet of which strength has been enhanced compared to the existing dry-coated tablets.

Solution to Problem

A dry-coated tablet according to the present invention comprises an inner core and an outer layer which contains powdery solid components and with which the inner core is coated, wherein an opening is formed in the outer surface of the inner core, the opening is larger than the average particle size of a component the average particle size of which is the smallest of the powdery solid components contained in the outer layer, and the inner surface of the outer layer penetrates in the opening.

In such dry-coated tablets, the opening formed in the outer surface of the inner core is larger than the average particle size of a component the average particle size of which is the smallest of the powdery solid components contained in the outer layer. Accordingly, since at least one powdery solid component penetrates in the opening when an outer layer is provided, it is possible to enhance the strength of the dry-coated tablet.

An opening in the outer surface of the inner core is, for example, an opening of a recess formed in the inner core.

The depth of the recess may be larger than the average particle size of a component the average particle size of which is the smallest of the powdery solid components contained in the outer layer. In this case, it is possible to further enhance the strength of the dry-coated tablet.

Recesses may be formed as grooves, or may be formed as holes interspersed in the outer surface of the inner core. The recesses may be letters, figures, symbols and the like formed as grooves.

The inner core may have two surfaces arranged opposed to each other, and recesses may be formed in at least one of the two surfaces. In this case, it is possible to compress the outer layer along the opposite direction of the two surfaces to thereby allow the inner surface of the outer layer to penetrate in the recesses more securely.

The inner core may have two surfaces arranged opposed to each other and a circumferential surface arranged between the circumferential edges of the two surfaces, and recesses may be formed in the circumferential surface.

An opening in the outer surface of the inner core may be an opening of a through-hole formed in the inner core.

The inner core has two surfaces arranged opposed to each other, and the through-hole may be formed so as to connect the two surfaces. In this case, it is possible to compress the outer layer along the opposite direction of the two surfaces to thereby allow the inner surface of the outer layer to penetrate in the through-hole more securely.

At least one of the inner core and the outer layer may contain an active component.

The inner core and the outer layer may each contain a same or different active component. In this case, by the action of the active component contained in the outer layer, it is possible to enhance the effect of the active component in the inner core, to suppress the specific action of the active component in the inner core, and the like.

The active component contained in the outer layer may form granules together with components other than the active component.

Although the active component contained in the inner core and the active component contained in the outer layer are not particularly limited, the active component contained in the inner core may be acetylsalicylic acid and the active component contained in the outer layer may be a proton pump inhibitor, for example. In this case, acetylsalicylic acid, which achieves anti-inflammatory action, is supplied in the body of a recipient while the proton pump inhibitor, which reduces the load on the stomach and duodenum associated with the ingestion of acetylsalicylic acid, is supplied in the body of the recipient.

The inner core may have an uncoated tablet and a coating layer coating the uncoated tablet.

It is preferable that the friability of the inner core or the friability of the uncoated tablet of the inner core be 1% or less.

Advantageous Effects of Invention

According to the present invention, it is possible to provide a dry-coated tablet of which strength has been enhanced compared to the existing dry-coated tablets.

DESCRIPTION OF EMBODIMENTS

Figure 1:
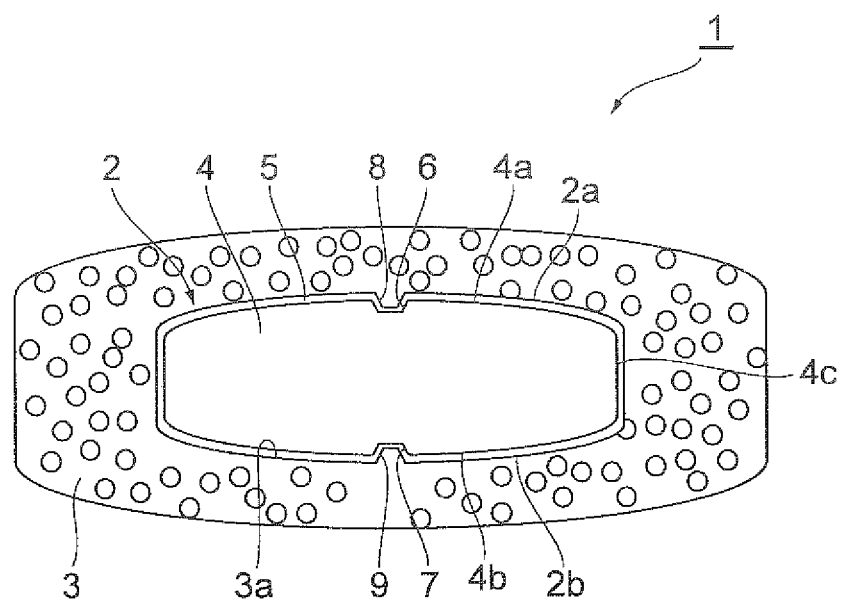
FIG. 1 is a schematic view showing a dry-coated tablet according to a first embodiment.
Figure 2:
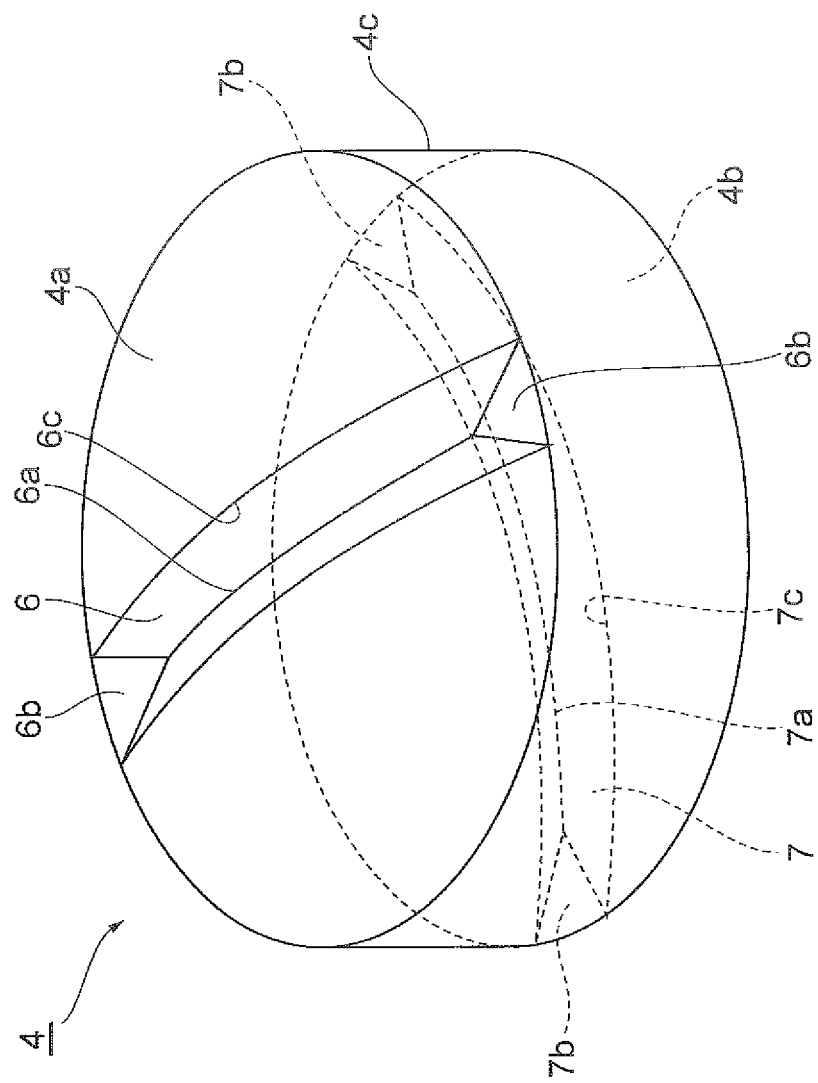
FIG. 2 is a perspective view of an uncoated tablet of an inner core.
Figure 3:
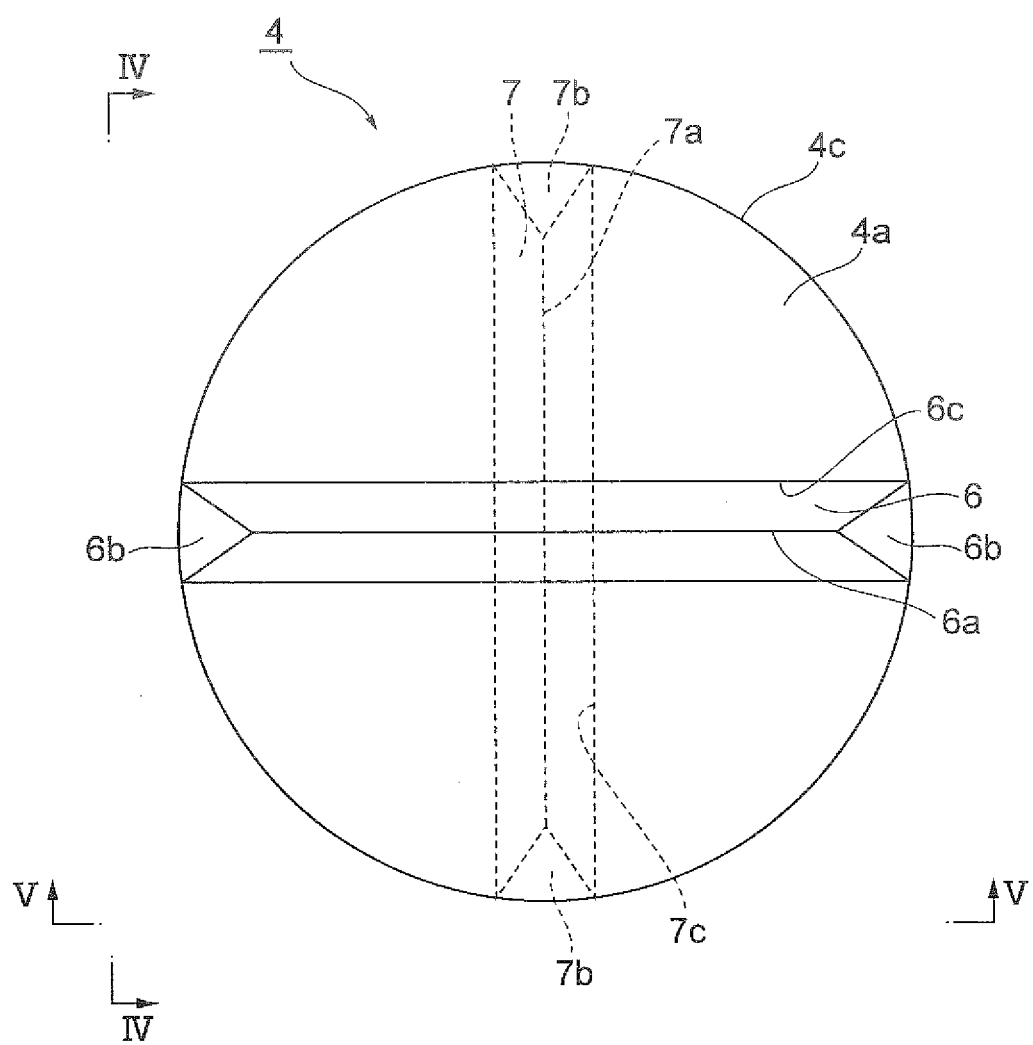
FIG. 3 is a plan view of the uncoated tablet of the inner core.

Hereinafter, preferable embodiments of the present invention will be described in detail with referring to the drawings. In the drawings, the same reference numerals are given to identical or equivalent elements, and overlapping description will be omitted.

First Embodiment

A dry-coated tablet 1 shown in FIG. 1 has an inner core 2 and an outer layer 3 with which the inner core 2 is coated. The dry-coated tablet 1 is a tablet to supply acetylsalicylic acid, which achieves anti-inflammatory action, and a proton pump inhibitor, which reduces the load on the stomach and duodenum associated with the ingestion of acetylsalicylic acid, in the body of a recipient. Acetylsalicylic acid, which is an active component, is contained in the inner core 2, and the proton pump inhibitor, which is an active component, is contained in the outer layer 3. The tablet weight of the dry-coated tablet 1 is from about 350 mg to about 550 mg. In order to maintain the physical strength of the tablet, it is preferable that the weight ratio between the inner core 2 and the outer layer 3 be from about 1:2 to about 1:6 and it is more preferable that the ratio be from about 1:2 to about 1:4.

As shown in FIG. 1, the inner core 2 has an uncoated tablet containing acetylsalicylic acid 4 and a coating layer 5 which contains an enteric component and with which the uncoated tablet 4 is coated. Accordingly, it is possible to protect the uncoated tablet 4 with the coating layer 5 after the outer surface of the inner core 2 is exposed in the body of a recipient to thereby supply acetylsalicylic acid in the inner core 2 deeper into the body of a recipient. Hereinafter, "coating" is not limited to coating the whole surface of an object, includes the case of partially coating, and is intended to include the case of being adsorbed or absorbed on the surface of the object.

It is preferable that the content of acetylsalicylic acid in the uncoated tablet 4 be about 70 to about 400 mg. In the case where the dry-coated tablet 1 is intended to suppress mainly pain, fever, and inflammation as a non-steroidal anti-inflammatory drug (NSAID), it is preferable that the content of acetylsalicylic acid in the uncoated tablet 4 be from about 250 to about 400 mg. In the case where the dry-coated tablet 1 is intended to suppress thrombosis, embolization, and the like in diseases in the cerebral blood vessel and circulatory organ regions, it is preferable that the content of acetylsalicylic acid in the uncoated tablet 4 be about 70 to about 120 mg, and it is more preferable that the content be about 100 mg.

It is possible for the uncoated tablet 4 to contain additives other than acetylsalicylic acid, such as excipients, disintegrating agents, fluidizers, binders, surfactants, and lubricants. Although it is not always necessary for the uncoated tablet 4 to contain all these additives, it is preferable that it contain at least an excipient, a disintegrating agent, and a binder. The uncoated tablet 4 may further contain other additives.

Examples of the excipient include lactose, white sugar, D-mannitol, starch, corn starch, crystalline cellulose, and light anhydrous silicic acid. Any one of these excipients may be used singly, or two or more may be used in combination. It is preferable that the content of the excipient in the inner core 2 be from about 5 to about 30% by weight, and it is more preferable that the content be from about 10 to about 20% by weight.

Examples of the disintegrating agent include carboxymethyl cellulose (carmellose), croscarmellose sodium, crystalline cellulose, pregelatinized starch, gelatin, and low-substituted hydroxypropyl cellulose. At least one of these disintegrating agents may be used singly, or two or more may be used in combination. From the viewpoint of enhancing the disintegratability and stability of acetylsalicylic acid, it is particularly preferable to use carboxymethyl cellulose. It is preferable that the content of the disintegrating agent in the inner core 2 be from about 1 to about 20% by weight, and it is more preferable that the content be from about 1 to about 10% by weight.

Examples of the fluidizer include light anhydrous silicic acid, hydrated silicon dioxide, talc, and stearic acid. At least any one of these fluidizers may be used singly, or two or more may be used in combination. It is preferable that the content of the fluidizer in the inner core 2 be from 0 to about 10% by weight.

Examples of the binder include hydroxypropyl cellulose, corn starch, hydroxypropyl methylcellulose, crystalline cellulose, pregelatinized starch, polyvinyl pyrrolidone, acacia gum powder, gelatin, pullulan, and low-substituted hydroxypropyl cellulose. It is preferable that the content of the binder in the inner core 2 be from 0 to about 5% by weight.

Examples of the surfactant include sodium lauryl sulfate, polyoxyethylene polyoxypropylene glycol, and polysorbate 80. Examples of the lubricant include hydrogenated oils, sodium lauryl sulfate, stearic acid, and polysorbate 80.

The uncoated tablet 4 is formed by tableting a mixed powder which has been obtained by mixing an acetylsalicylic acid powder and an additive powder. After a premixed product comprising acetylsalicylic acid and an excipient is obtained, other additives may be added to the premixed product to thereby obtain mixed powder. Examples of the premixed product include dry granulated products containing acetylsalicylic acid and corn starch at a weight ratio of 90:10. A mixed powder may be obtained by mixing the acetylsalicylic acid granulated product with additives, after an acetylsalicylic acid granulated product of which grain size is coarse is obtained. It is preferable that 80% by weight or more of the whole acetylsalicylic acid form an acetylsalicylic acid granulated product of which particle size is from about 125 to about 1000 μm. The amount of acetylsalicylic acid which forms an acetylsalicylic acid granulated product of which particle size is from about 125 to about 1000 μm can be measured using screens of which openings are 125 μm and 1000 μm, for example.

The mixed powder is obtained by mixing methods generally used, for example, mixing, kneading, and granulating. Examples of the equipment used for mixing, kneading, and granulating include Vertical Granulator VG10 (manufactured by Powrex Corporation), universal kneaders (manufactured by HATA IRON WORKS CO., LTD.), fluidized bed granulators LAB-1, FD-3S, and FD-WSG-60 (manufactured by Powrex Corporation), V-shaped mixers, and tumbler mixers.

The uncoated tablet 4 can be obtained by tableting using equipment such as single punch tablet presses and rotary tablet presses (manufactured by KIKUSUI SEISAKUSHO LTD.). It is preferable that tableting pressure be from 1 to 80 kN/cm$^2$, for example, it is more preferable that the pressure be from 5 to 50 kN/cm$^2$, and it is particularly preferable that the pressure be from 8 to 25 kN/cm$^2$. It is preferable that the rotating speed in the case where a rotary tablet press is used be, for example, from 3 to 80 rpm, it is more preferable that the rotating speed be from 3 to 60 rpm, and it is particularly preferable that the rotating speed be from 5 to 40 rpm.

The coating layer 5 with which the uncoated tablet 4 is coated can contain aqueous enteric polymer bases, sustained release bases, water-soluble polymers, and plasticizers as enteric components. It is not always necessary that the coating layer 5 contain all of these enteric components.

Examples of the aqueous enteric polymer base include cellulose acetate phthalate (CAP), hydroxypropyl methylcellulose phthalate (HP-55), hydroxymethyl cellulose acetate succinate, (meta)acrylic acid copolymers [such as methacrylic acid copolymer LD (Eudragit L30D-55 (trade name; manufactured by Evonik Co., Ltd.)], Kollicoat MAE30DP (trade name; manufactured by BASF Corporation), and POLYQUID PA30 (trade name; manufactured by Sanyo Chemical Industries, Ltd.)], carboxymethyl ethyl cellulose, and shellac. Although any one of these aqueous enteric polymer bases may be used singly, or two or more may be used in combination, it is preferable to use (meth) acrylic acid copolymers such as methacrylic acid copolymer LD. It should be noted that description of "(meth)acrylic" means acrylic or methacrylic and the same applies to similar expressions such as (meth)acrylate.

Examples of the sustained release base include (meth) acrylate copolymers etc. [such as ethyl acrylate-methyl methacrylate copolymers (Eudragit NE30D (trade name; manufactured by Evonik Co., Ltd.)), aminoalkyl methacrylate copolymer RS (Eudragit RL30D (trade name; manufactured by Evonik Co., Ltd.)), and aminoalkyl methacrylate copolymer RS (Eudragit RS30D (trade name; manufactured by Evonik Co., Ltd.)) etc.]. Although any one of these sustained release bases may be used singly, or two or more may be used in combination, it is preferable to use (meth) acrylate copolymers such as ethyl acrylate.methyl methacrylate copolymers. It is preferable that the ratio of the content of the sustained release base to the content of the aqueous enteric polymer base be from about 5 to about 30% by weight, and it is more preferable that the ratio be from about 5 to 15% by weight.

Examples of the water-soluble polymer include ethanol-soluble water-soluble polymers (cellulose derivatives (such as hydroxypropyl cellulose (HPC)) and polyvinyl pyrrolidone), non-ethanol-soluble water-soluble polymers (cellulose derivatives (such as hydroxypropyl methylcellulose (HPMC), methyl cellulose, sodium carboxymethyl cellulose), sodium polyacrylate, polyvinyl alcohol, sodium alginate, and guar gum). At least any one of these water-soluble polymers may be used singly, or two or more may be used in combination.

Examples of the plasticizer include triethyl citrate, polyethylene glycol, acetylated monoglyceride, triacetylene, and castor oil. At least any one of these plasticizers may be used singly, or two or more may be used in combination. It is preferable that the content of the plasticizer in a coating agent be from 1 to about 30% by weight.

In order to more securely prevent breakage of the uncoated tablet 4 in dry-coated tableting of the outer layer 3 described below, it is preferable that the coating layer 5 contain at least an aqueous enteric polymer base and a sustained release base, and it is particularly preferable that the coating layer 5 contain (meth)acrylic acid copolymers such as methacrylic acid copolymer LD and (meth)acrylate copolymers such as ethyl acrylate.methyl methacrylate copolymer in a predetermined proportion. For example, it is preferable that the coating layer 5 contain (meth)acrylic acid copolymers such as methacrylic acid copolymer LD and (meth)acrylate copolymers such as ethyl acrylate.methyl methacrylate copolymer in a weight ratio of about 85:15 to about 95:5, and it is more preferable that the coating layer 5 contain (meth)acrylic acid copolymers such as methacrylic acid copolymer LD and (meth)acrylate copolymers such as ethyl acrylate.methyl methacrylate copolymer in a weight ratio of 9:1.

The coating layer 5 may further contain additives such as surfactants and lubricants. Examples of the surfactant include polysorbate, polyoxyethylene.polyoxypropylene copolymer, and sodium lauryl sulfate, and of these, polysorbate and sodium lauryl sulfate are preferred. Examples of the lubricant include talc and glycerin monostearate, and of these, glycerin monostearate is preferred. The coating layer 5 may be formed of a plurality of layers of which components contained are different from one another.

The proportion of the weight of the coating layer 5 to the weight of the uncoated tablet 4 can be set as appropriate from the viewpoint of the acid resistance and elutability of acetylsalicylic acid, and it is preferable that the proportion be, for example, from about 3 to about 30% by weight, and it is more preferable that the proportion be about 5 to about 20% by weight.

The coating layer 5 can be formed by coating the surface of the uncoated tablet 4 with a coating liquid in which an aqueous enteric polymer base, a sustained release base, water-soluble polymer, a plasticizer, a surfactant, and the like are mixed, for example, by a common coating method a method using a coating device such as film coating devices. The coating liquid may be a solution or dispersion liquid and is made using organic solvents such as ethanol, water or mixture of these as the solvent. The concentration of the component constituting the coating layer 5 in the coating liquid is, for example, from about 0.1 to about 50% by weight, and from about 5 to about 30% by weight is preferred.

Subsequently, the outer layer 3 will be described. The outer layer 3 can contain a proton pump inhibitor (PPI). As the PPI, those selected from benzimidazole compounds having antitumor action such as lansoprazole, omeprazole, rabeprazole, and pantoprazole and optically active substances thereof and pharmaceutically acceptable salts thereof are particularly preferred.

In the outer layer 3, a PPI can form enteric fine granules (hereinafter, PPI enteric fine granules) together with other components. Accordingly, it is possible to make the PPI, which is the active component, act more effectively. Specifically, a composition containing a PPI (hereinafter, a PPI composition) can form fine granules coated with an enteric coating layer. It is preferable that the average particle size of the PPI enteric fine granules be about 400 μm or less, and it is more preferable that the average particle size be about 300 to about 400 μm. The "average particle size" of the PPI enteric fine granules refers to a median diameter based on volume (a median diameter: a particle size corresponding to 50% of the cumulative distribution). Examples of the measuring method include laser diffraction particle size distribution measurement, and specific examples include a method using a laser diffraction particle size distribution analyzer HEROS RODOS (manufactured by Sympatec GmbH (Germany)).

It is preferable that the maximum particle size of the PPI enteric fine granules be substantially 425 μm or less, it is more preferable that the maximum particle size be substantially 400 μm or less, it is more preferable that the maximum particle size be substantially from about 300 to about 425 μm, and it is particularly preferable that the maximum particle size be substantially from about 300 to about 400 μm. The meaning of "substantially" means that a small amount (about 5% by weight or less) of particles having a particle size outside each range may be contained as long as the particles are inevitably mixed.

It is preferable that the content of the PPI in the PPI composition before coated with an enteric coating layer be, for example, about 5% by weight or more, it is more preferable that the content be from about 10 to about 50% by weight, it is more preferable that the content be from about 15 to about 50% by weight, and it is particularly preferable that the content be from about 20 to about 50% by weight. It is preferable that the content of the PPI in the whole dry-coated tablet 1 be, for example, about 1% by weight or more, it is more preferable that the content be from about 1.5 to about 10.0% by weight, and it is particularly preferable that the content be from about 2.0 to about 8.0% by weight. The PPI enteric fine granules can be obtained in accordance with the method described in Japanese Patent Application Laid-Open No. 2000-281564 or the methods in accordance therewith.

It is possible that the outer layer 3 contains additives in addition to the PPI enteric fine granules. It is preferable that the content of the PPI enteric fine granules in the outer layer 3 be from about 30 to about 70% by weight, and it is more preferable that the content be from about 30 to about 60% by weight. It is possible that the outer layer 3 contains at least one (preferably from one to five) excipients or disintegrating agents as the additives. The outer layer 3 may further contain binders, acidulants, artificial sweeteners, fragrances, lubricants, colorants, stabilizers, and the like.

Examples of the excipient include water-soluble sugar alcohols, lactose, white sugar, D-mannitol, starch, corn starch, crystalline cellulose, light anhydrous silicic acid, and magnesium aluminometa silicate. In order to enhance the strength of the dry-coated tablet, it is preferable that the excipient contain at least one selected from crystalline cellulose and magnesium aluminometa silicate.

Water-soluble sugar alcohol means a sugar alcohol by which the amount of water required is less than 30 ml when 1 g of the sugar alcohol is added to water and vigorously shaken for 30 seconds at 20° C. every five minutes to thereby be dissolved within 30 minutes. Examples of the water-soluble sugar alcohol include sorbitol, mannitol, maltitol, reduced saccharified starch, xylitol, reduced palatinose, and erythritol. Of these water-soluble sugar alcohols, two or more (preferably two or three) may be mixed and used as appropriate. It is preferable that the water-soluble sugar alcohol be mannitol, xylitol, or erythritol, it is more preferable that the water-soluble sugar alcohol be mannitol or erythritol, and it is particularly preferable that the water-soluble sugar alcohol be mannitol. Examples of erythritol include those which are produced by fermentation with yeast usually using glucose as the raw material and of which grain size is 50 mesh or less. It is possible to obtain erythritol as commercial products [Nikken Chemicals Co., Ltd. and the like].

Examples of the crystalline cellulose include those obtained by partially depolymerizing and purifying α-cellulose. Those called microcrystalline cellulose may also be included in the crystalline cellulose. Specific examples of the crystalline cellulose include CEOLUS KG 802, CEOLUS KG 1000, CEOLUS PH 101, CEOLUS PH 102, CEOLUS PH 301, CEOLUS PH 302, and CEOLUS RC-591 (crystalline cellulose-carmellose sodium). Of these, CEOLUS KG 1000 is particularly preferred. Although any one of these crystalline celluloses may be used singly, two or more (preferably two or three) may be used in combination. It is possible to obtain these crystalline celluloses as commercial products [manufactured by Asahi Kasei Corporation].

Specific examples of the magnesium aluminometa silicate include Neusilin FH1, Neusilin FL1, Neusilin NFL2N, and Neusilin UFL2, and Neusilin UFL2 is preferred. One of these magnesium aluminometa silicates may be used singly, or two or more (preferably two or three) may be used in combination. It is possible to obtain these magnesium aluminometa silicates as commercial products [manufactured by Fuji Chemical Industry Co., Ltd.].

Examples of the disintegrating agent include disintegrating agents commonly used in the formulation field, such as crospovidone (e.g., Kollidon CL-F); disintegrating agents called super disintegrating agents, such as croscarmellose sodium (FMC-Asahi Kasei Corporation), and carmellose calcium (GOTOKU CHEMICAL COMPANY LTD); sodium carboxymethyl starch (e.g., manufactured by Matsutani Chemical Industry Co., Ltd.); low-substituted hydroxypropyl cellulose (e.g., manufactured by Shin-Etsu Chemical Co., Ltd.); and corn starch.

Crospovidone may be any crosslinked polymers having the chemical name of 1-ethenyl-2-pyrrolidinone homopolymer, including those called polyvinyl pyrrolidone (PVPP) and 1-vinyl-2-pyrrolidinone homopolymer, and specific examples include Kollidon CL (manufactured by BASF Corporation), Kollidon CL-F (manufactured by BASF Corporation), Polyplasdone XL (manufactured by ISP), Polyplasdone XL-10 (manufactured by ISP), and Polyplasdone INF-10 (manufactured by ISP). The molecular weight of crospovidone usually exceeds 1000000.

Examples of the binder include hydroxypropyl cellulose, hydroxypropyl methylcellulose, crystalline cellulose, pregelatinized starch, polyvinyl pyrrolidone, acacia gum powder, gelatin, pullulan, and low-substituted hydroxypropyl cellulose. Examples of the acidulant include citric acid (citric acid anhydride), tartaric acid, and malic acid. Examples of the artificial sweetener include sodium saccharin, dipotassium glycyrrhizate, aspartame, stevia, and thaumatin. The fragrance may be any of synthetic and natural fragrances, and specific examples include lemon, lime, orange, menthol, and strawberry. Examples of the lubricant include magnesium stearate, sucrose fatty acid esters, polyethylene glycol, talc, stearic acid, and hydrogenated oils. Examples of the colorant include food dyes such as food yellow No. 5, food red No. 2, and food blue No. 2; food lake dyes; colcothar, and yellow ferric oxide. Examples of the stabilizer include basic inorganic salts such as sodium carbonate, sodium hydrogen carbonate, potassium carbonate, potassium hydrogen carbonate, heavy magnesium carbonate, magnesium carbonate, magnesium oxide, magnesium hydroxide, magnesium aluminometa silicates, magnesium silicate, magnesium aluminate, synthetic hydrotalcite [$Mg_6Al_2(OH)_{16}.CO_3.4H_2O$] and alumina magnesium hydroxide [$2.5MgO.Al_2O_3.xH_2O$].

The outer layer 3 is formed by mixing PPI enteric fine granules and additives in a known method to obtain outer layer mixed powder, coating the inner core 2 with the outer layer mixed powder, and carrying out tableting (hereinafter, tableting of the outer layer 3 is called "dry-coated tableting".). When the PPI enteric fine granules and additives are mixed, it is preferable that, after the PPI enteric fine granules and the excipient are mixed, granulation be carried out with spraying a binder as required to obtain outer layer granulated powder, and the powder be mixed with other additives to thereby obtain outer layer mixed powder. In this way, the tablet strength and the acid resistance of the dry-coated tablet 1 are enhanced.

It is preferable that the additive used for granulation of the outer layer granulated powder (hereinafter, referred to as "the additive for granulation") contain a water-soluble sugar alcohol, it is preferable that the content be an amount from about 10 to about 95% by weight relative to the total amount of the additives contained in the outer layer 3, and it is more preferable that the content be an amount from about 20 to about 70% by weight. It is preferable that the additive for granulation further contain crystalline cellulose, it is preferable that the content be an amount from about 1 to about 50% by weight relative to the amount of the additive for granulation contained in the outer layer 3, and it is more preferable that the content be an amount from about 2 to about 15% by weight. In the case where the additive for granulation contains a binder, it is preferable that the content be an amount from about 2 to about 15% by weight relative to the amount of the additive for granulation contained in the outer layer 3, and it is more preferable that the content be an amount from about 2 to about 10% by weight.

When the outer layer mixed powder is obtained, it is preferable that the additive to be mixed with the outer layer granulated powder (hereinafter, the additive for mixing) contain, for example, excipients such as crystalline cellulose and magnesium aluminometa silicate, it is preferable that the content be an amount from about 5 to about 30% by weight relative to the total amount of the outer layer mixed powder, and, it is more preferable that the content be from about 5 to about 20% by weight. It is more preferable that the additive for mixing contain magnesium aluminometa silicate, it is preferable that the content be an amount from about 1 to about 15% by weight relative to the total amount of the outer layer mixed powder, and it is more preferable that the content be an amount from about 1 to about 10% by weight. It is preferable that the additive for mixing further contain a disintegrating agent such as crospovidone, it is preferable that the content be an amount from about 1 to about 20% by weight relative to the total amount of the outer layer mixed powder, and it is more preferable that the content be an amount from about 1 to about 10% by weight. It is preferable that the additive for mixing further contain a lubricant such as magnesium stearate, it is preferable that that the content be an amount from about 0.1 to about 10% by weight relative to the total amount of the outer layer mixed powder, and it is more preferable that the content be an amount from about 0.1 to about 5% by weight.

It is possible to produce the outer layer granulated powder by known granulation methods such as tumbling granulation methods (such as centrifugal tumbling granulation methods), fluidized bed granulation methods (such as tumbling fluidized bed granulation and fluidized bed granulation), and stirring granulation methods, and of these granulation methods, the fluidized bed granulation method is preferred. It is possible to carry out mixing of PPI enteric fine granules and an excipient before formation of the outer layer granulated powder and mixing when the outer layer mixed powder is obtained in accordance with mixing methods commonly used. Examples of the equipment used for mixing these include Vertical Granulator VG10 (manufactured by Powrex Corporation), fluidized bed granulators LAB-1, FD-3S, and FD-WSG-60 (manufactured by Powrex Corporation), FLO-5M (manufactured by Freund Corporation), V-shaped mixers, and tumbler mixers.

Dry-coated tableting is obtained by tableting using equipment such as single punch tablet presses such as Autograph (manufactured by KIKUSUI SEISAKUSHO LTD.) or rotary dry-coated tablet presses (manufactured by KIKUSUI SEISAKUSHO LTD.). It is preferable that tableting pressure be from 1 to 40 $kN/cm^2$, it is more preferable that the pressure be from 5 to 30 $kN/cm^2$, and it is particularly preferable that the pressure be from 10 to 30 $kN/cm^2$. It is preferable that the rotating speed in the case where a rotary tablet press is used be from 3 to 40 rpm, it is more preferable that the rotating speed be from 3 to 30 rpm, and it is particularly preferable that the rotating speed be from 8 to 25 rpm.

The temperature of the raw material powder or particles on dry-coated tableting is equivalent to, for example, room temperature. Room temperature refers to the temperature in the room where tableting is carried out in manufacture of common tablets, and the temperature is usually from about 20 to about 23° C. After dry-coated tableting, the dry-coated tablet 1 may be dried as required. It is possible to carry out this drying by, for example, drying methods common in the formulation such as vacuum drying and fluidized bed drying. It is possible to further form a film layer outside the tablet subjected to dry-coated tableting.

Since the dry-coated tablet 1 described hereinabove includes a PPI, it has excellent antitumor action, gastric secretion inhibitory action, mucosal protective action, anti-*helicobacter pylori* action, and the like. Since the dry-coated tablet 1 includes acetylsalicylic acid, it is useful for suppression of thrombosis and embolization in diseases of cerebral blood vessels and circulatory organ regions, for example, angina pectoris (chronic stable angina pectoris and unstable angina pectoris) and myocardial infarction; prevention and treatment of ischemic cerebrovascular disorders (transient ischemic attacks (TIA) and cerebral infarction); suppression of thrombosis and embolization after implementation of coronary artery bypass grafting (CABG) or percutaneous transluminal coronary angioplasty (PTCA); and prevention and treatment of Kawasaki disease (including cardiovascular sequelae in Kawasaki disease). Accordingly, it is possible to administer dry-coated tablets of the present invention with a purpose of treating gastric ulceration or duodenal ulceration or suppressing the onset thereof, while continuing aspirin administration. In the case where prevention and treatment of such diseases are intended, as the PPI, about 10 mg to about 40 mg per day is administered, and as acetylsalicylic acid, (a dosage as low as) about 70 mg to about 120 mg per day is administered.

It is possible to employ acetylsalicylic acid as one of non-steroidal anti-inflammatory drugs (NSAIDs) also for treatment of, mainly, pain, fever, and inflammation. Gastric ulceration or duodenal ulceration may be caused by NSAIDs, and there may be a case where it is difficult to cease administration of NSAIDs because QOL is significantly decreased particularly in treatment of rheumatoid arthritis and osteoarthritis. In such cases, it is possible to administer dry-coated tablets of the present invention with a purpose of treating gastric ulceration or duodenal ulceration or suppressing the onset thereof, while continuing administration of NSAIDs. In the case where such treatment is intended, as the PPI, about 10 mg to about 40 mg per day is administered, and as acetylsalicylic acid, about 240 mg to about 400 mg per day is administered. Accordingly, the dry-coated tablet 1 is useful as a low toxic and safe combination medicament of a PPI and acetylsalicylic acid.

It is possible to orally administer the dry-coated tablet 1 with a purpose of suppression of thrombosis and embolization in diseases of cerebral blood vessels and circulatory organ regions, treatment and prevention of ulceration caused by non-steroidal anti-inflammatory drugs, and the like in mammals (for example, humans, monkeys, sheep, horses, dogs, cats, rabbits, rats, and mice). In addition to the purpose described above, the dry-coated tablet 1 and penicillin antibiotics (for example, amoxicillin) and erythromycin antibiotics (for example, clarithromycin) may be used in combination in order to eliminate *Helicobacter pylori* or to aid the elimination. The daily dosage of the dry-coated tablets 1 varies depending on the degree of the symptom, the age, sex, and body weight of the subject to receive the administration, the timing and interval of the administration, and types of active components, and is not particularly limited. The dry-coated tablets 1 may be administered once a day or in two or three doses a day.

Subsequently, the shapes of the inner core 2 and the outer layer 3 are described in more detail. As shown in FIGS. 2 to 5, the uncoated tablet 4 of the inner core 2 exhibits a flat shape forming a circle in planar view. Specifically, the uncoated tablet 4 has circular surfaces 4a and 4b opposed to each other, and a circumferential surface 4c arranged between the circumferential edges of the circular surfaces 4a and 4b, and the distance between both ends of the uncoated tablet 4 in the opposite direction of the circular surfaces 4a and 4b (hereinafter, referred to as the "thickness") is smaller than the diameter of the uncoated tablet 4 in planer view. The circular surfaces 4a and 4b are each spherically expanded. In this way, the uncoated tablet 4 exhibits a tablet shape of a so-called circular R-face. The diameter of the uncoated tablet 4 in planer view is, for example, from about 5 to about 8 mm. The radius of curvature of the spherical surface formed by the circular surfaces 4a and 4b is larger than the radius of the uncoated tablet 4 in planer view, and is, for example about 10 mm.

In the circular surfaces 4a and 4b, grooves (recesses) 6 and 7 respectively along the radial direction of the circular surfaces 4a and 4b are formed. The grooves 6 and 7 intersect each other at right angles in planar view. Although it is not always necessary for the grooves 6 and 7 to intersect each other at right angles in planar view, it is preferable that they intersect each other in planar view. Each cross sectional shape of the grooves 6 and 7 is V-shaped, and the width of the grooves 6 and 7 becomes wider as further from the bottom. The bottoms 6a and 7a of the grooves 6 and 7 are curved along the spherical surface each formed by the circular surfaces 4a and 4b. End surfaces 6b and 6b, which correspond to a plane including the circumferential edge of the circular surface 4a, are formed at both ends of the groove 6, and end surfaces 7b and 7b, which correspond to a plane including the circumferential edge of the circular surface 4b, are formed at both ends of the groove 7. Openings 6c and 7c are each formed by the grooves 6 and 7 in the circular surfaces (outer surfaces of the uncoated tablet 4) 4a and 4b. The grooves 6 and 7 are formed with a tableting punch (mold) when the uncoated tablet 4 is tableted. It should be noted that recesses such as the grooves 6 and 7 are formed and the peripheries become a protrusion relatively. That is, providing a recess and providing a protrusion are synonymous.

Figure 4:
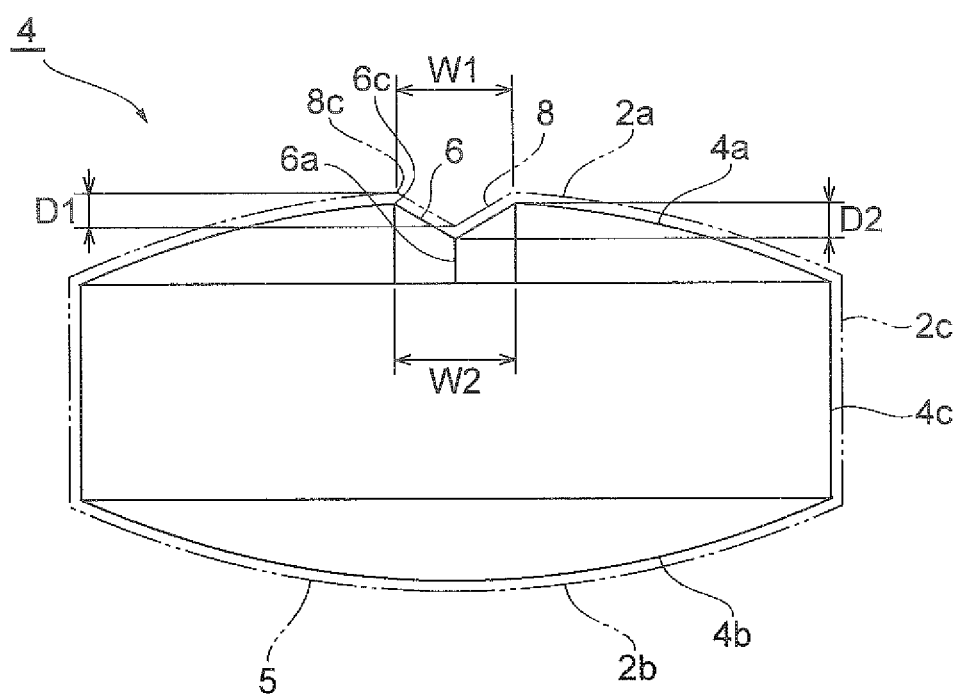
FIG. 4 is an arrow view taken along line IV-IV in FIG. 3.
Figure 5:
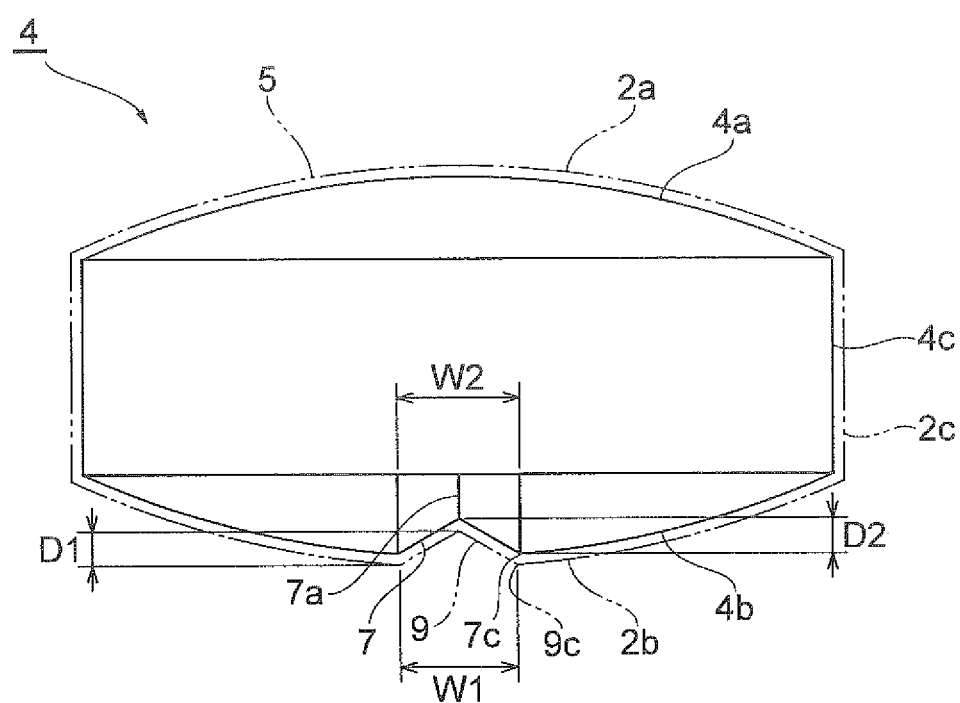
FIG. 5 is an arrow view taken along line V-V in FIG. 3.

The inner core 2 is composed by coating the outer surfaces of the uncoated tablet 4 with a coating layer 5, as described above. After the coating layer 5 is formed, the inner core 2 exhibits a flat shape forming a circle in planar view as does the uncoated tablet 4. As shown in FIG. 4 and FIG. 5, the circular surfaces 4a and 4b of the uncoated tablet 4 are coated with the coating layer 5 to thereby form circular surfaces 2a and 2b of the inner core 2. The circumferential surface 4c of the uncoated tablet 4 is coated with the coating layer 5 to thereby form the circumferential surface 2c of the inner core 2. The coating layer 5 penetrates in the grooves 6 and 7 of the uncoated tablet 4 to thereby form grooves 8 and 9 of which cross sections are V-shaped in the circular surfaces 2a and 2b of the inner core 2. Openings 8c and 9c are each formed by the grooves 8 and 9 in the circular surfaces (outer surfaces of the inner core 2) 2a and 2b. The size of the openings 8c and 9c in the inner core 2 (opening width) W1 is at least larger than the average particle size of a component the average particle size of which is the smallest of the powdery solid components contained in the outer layer 3. It is more preferable that the opening width W1 be larger than the average particle size of a component the average particle size of which is the largest of the powdery solid components contained in the outer layer 3.

It is preferable that the depth D1 of the grooves 8 and 9 in the inner core 2 be also larger than the average particle size of a component the average particle size of which is the smallest of the powdery solid components contained in the outer layer 3, and it is more preferable that the depth be larger than the average particle size of a component the average particle size of which is the largest of the powdery solid components contained in the outer layer 3.

The "average particle size" of each powdery solid component contained in the outer layer 3 means the median diameter based on volume (median diameter: a particle size corresponding to 50% of the cumulative distribution). Examples of the measuring method include laser diffraction particle size distribution measurement, and specific examples include a method using a laser diffraction particle size distribution analyzer HEROS RODOS (manufactured by Sympatec (Germany)).

The component the average particle size of which is the smallest of the powdery solid components contained in the outer layer 3 is, for example, magnesium stearate, the average particle size of which is, for example, from about 4 to about 20 µm. The component the average particle size of which is the largest of the powdery solid components contained in the outer layer 3 is, for example, lansoprazole enteric fine granules, of which average particle size is, for example, from about 300 to about 400 µm. Accordingly, if the opening width W1 of the grooves 8 and 9 in the inner core 2 is about 1.0 mm and the depth D1 is about 0.6 mm, for example, the opening width W1 and the depth D1 become larger than the average particle size of a component the average particle size of which is the smallest of the powdery solid components contained in the outer layer 3 and furthermore, become larger than the average particle size of a component the average particle size of which is the largest of the solid components contained in the outer layer 3.

It should be noted that it is not essential that the inner core 2 have the coating layer 5. When the inner core 2 does not have the coating layer 5, the conditions described above concerning the opening width W1 and the depth D1 are applied to the opening width W2 and the depth D2 of the grooves 6 and 7.

If recesses such as grooves 8 and 9 are formed, peripheries of the recesses tend to lack strength compared to other flat portions. In the case where the strength in the peripheries of the recesses is lacking, there is a fear that the peripheries of the recesses are damaged when the uncoated tablet is fed to the next step or in the film step that follows. Thus, it is necessary for the peripheries of the recesses to have sufficient strength, and it is preferable that the recesses such as grooves 8 and 9 be formed such that the friability of the inner core 2 is 1% or less. It should be noted that it is possible to measure the friability in accordance with the friability testing method in the Japanese Pharmacopoeia. Furthermore, it is preferable that the recesses such as the grooves 6 and 7 be formed such that the friability of the uncoated tablet 4 is 1% or less before formation of the coating layer 5.

As shown in FIG. 1, the outer layer 3 is formed so as to allow the inner core 2 to be covered, and exhibits a flat shape corresponding to the shape of the inner core 2. The grooves 8 and 9 are filled with the components contained in the outer layer 3. That is, the inner surface 3a of the outer layer 3 penetrates in the grooves 8 and 9. On the surface of the outer layer 3, which is smooth, no grooves corresponding to the grooves 8 and 9 are formed. It is preferable that the outer diameter of the outer layer 3 in planer view, that is, the outer diameter of the dry-coated tablet 1 in planer view be larger than the outer diameter of the inner core 2 by 2 mm or more, for example, the outer diameter of the outer layer 3 is from about 8 to about 11 mm, from the viewpoint of securing the strength of the dry-coated tablet 1.

As described above, the outer layer 3 is formed by dry-coated tableting. Since the openings 8c and 9c in the outer surface of the inner core 2 is larger than the average particle size of a component the average particle size of which is the smallest of the powdery solid components contained in the outer layer 3, at least one powdery solid component contained in the outer layer 3 penetrates in the openings 8c and 9c so as not to form a gap in the grooves 8 and 9 when dry-coated tableting is carried out. Thus, the grooves 8 and 9 are securely filled with the powdery solid components contained in the outer layer 3. That is, the inner surface 3a of the outer layer 3 securely penetrates in the openings 8c and 9c, and the inner core 2 and the outer layer 3 are brought into a fitted state. Accordingly, since the inner core 2 and the outer layer 3 become difficult to peel from each other, it is possible to enhance the strength of the dry-coated tablet 1.

In the dry-coated tablet 1, the uncoated tablet 4 of the inner core 2 is coated with the coating layer 5. If the uncoated tablet 4 is coated with the coating layer 5, the surface of the inner core 2 is smoothed, and the adhesion between the inner core 2 and the outer layer 3 may become insufficient and easily peeled from each other. In such cases, the effectivity to provide the openings 8c and 9c in the outer surface of the inner core 2 to thereby enhance the strength of the dry-coated tablet 1 will be more marked.

In the case where the openings 8c and 9c in the outer surface of the inner core 2 is larger than the average particle size of a component the average particle size of which is the largest of the powdery solid components contained in the outer layer 3, the grooves 8 and 9 is more securely filled with the powdery solid components contained in the outer layer 3.

In the case where the depth D1 of the grooves 8 and 9 in the inner core 2 is larger than the average particle size of a component the average particle size of which is the smallest of the powdery solid components contained in the outer layer 3, the inner surface 3a of the outer layer 3 penetrates deeper in the inner core 2.

In the case where the depth D1 of the grooves 8 and 9 in the inner core 2 is larger than the average particle size of a component the average particle size of which is the largest of the powdery solid components contained in the outer layer 3, the inner surface 3a of the outer layer 3 penetrates further deeper in the inner core 2.

In the case where the friability of the inner core 2 is 1% or less, since loss of the grooves 8 and 9 due to abrasion is suppressed, it is possible to more securely enhance the strength of the dry-coated tablet. In the case where the friability of the uncoated tablet 4 is 1% or less, since loss of the grooves 6 and 7 due to abrasion of the uncoated tablet 4 is suppressed, it is possible to further securely enhance the strength of the dry-coated tablet.

The grooves 8 and 9 are provided in the circular surfaces 2a and 2b of the inner core 2. The inner core 2 exhibits a flat shape, and thus, the proportion of the area of the circular surfaces 2a and 2b of the inner core 2 in the surface area is large. Accordingly, since the effect to make the inner core 2 and the outer layer 3 difficult to peel off from each other is exerted over a wider area, it is possible to further enhance the strength of the dry-coated tablet 1. Dry-coated tableting of the outer layer 3 is carried out usually along the opposite direction of the circular surfaces 2a and 2b of the inner core 2, that is to say, of the two surfaces opposed to each other so as to compress the components in the outer layer 3. Thus, if the grooves 8 and 9 are formed in the two surfaces opposed to each other, the pressure of tableting becomes easy to act toward the inside of the grooves 8 and 9, making it possible to allow the inner surface 3a of the outer layer 3 to penetrate into the openings 8c and 9c more securely.

Since the width of the grooves 8 and 9 becomes wider as further from the bottom, the components in the outer layer 3 are easy to introduce from the opening to the bottom. Thus, it is possible to allow the inner surface 3a of the outer layer 3 to penetrate into the grooves 8 and 9 more securely.

The grooves 8 and 9 intersect each other in planar view. If recesses such as the grooves 8 and 9 have been formed here, the inner surface 3a of the outer layer 3 penetrates in the recesses, and the inner core 2 and the outer layer 3 become difficult to misalign from each other. This also contributes to enhancing the strength of the dry-coated tablet 1. In the case where the recesses are the grooves 8 and 9, misalignment of the inner core 2 and the outer layer 3 is effectively prevented in the direction intersecting the grooves 8 and 9. If the grooves 8 and 9 intersect each other in planar view, each radial direction of the inner core 2 intersects at least one of the grooves 8 and 9. Thus, misalignment of the inner core 2 and the outer layer 3 is effectively prevented in each radial direction of the inner core 2. If the grooves 8 and 9 intersect each other at right angles in planar view, it is possible to obtain the action to prevent misalignment of the inner core 2 and the outer layer 3 more uniformly in each radial direction of the inner core 2.

It should be noted that it is not always necessary to provide recesses of the same configuration as the grooves 8 and 9 in the inner core 2. At least openings may be formed in the outer surface of the inner core, wherein the openings are larger than the average particle size of a component the average particle size of which is the smallest of the powdery solid components contained in the outer layer 3. Examples of recesses of other embodiments will be described hereinafter.

Figure 6:
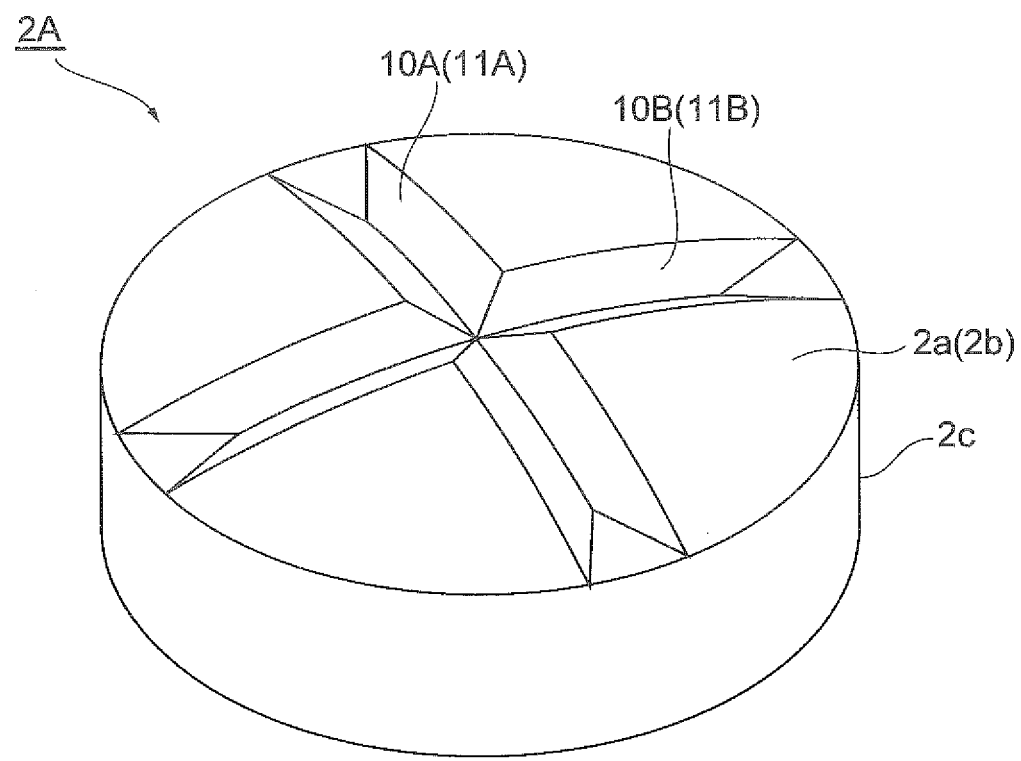
FIG. 6 is a perspective view showing a modified embodiment of the uncoated tablet of the inner core.

An inner core 2A shown in FIG. 6 is an inner core in the circular surface 2a of which grooves 10A and 10B are provided along the cross lines intersecting in the center of the surface and also in the circular surface 2b of which similar grooves 11A and 11B are provided. The grooves 10A and 10B and the grooves 11A and 11B may be inclined to each other in planar view.

Figure 7:
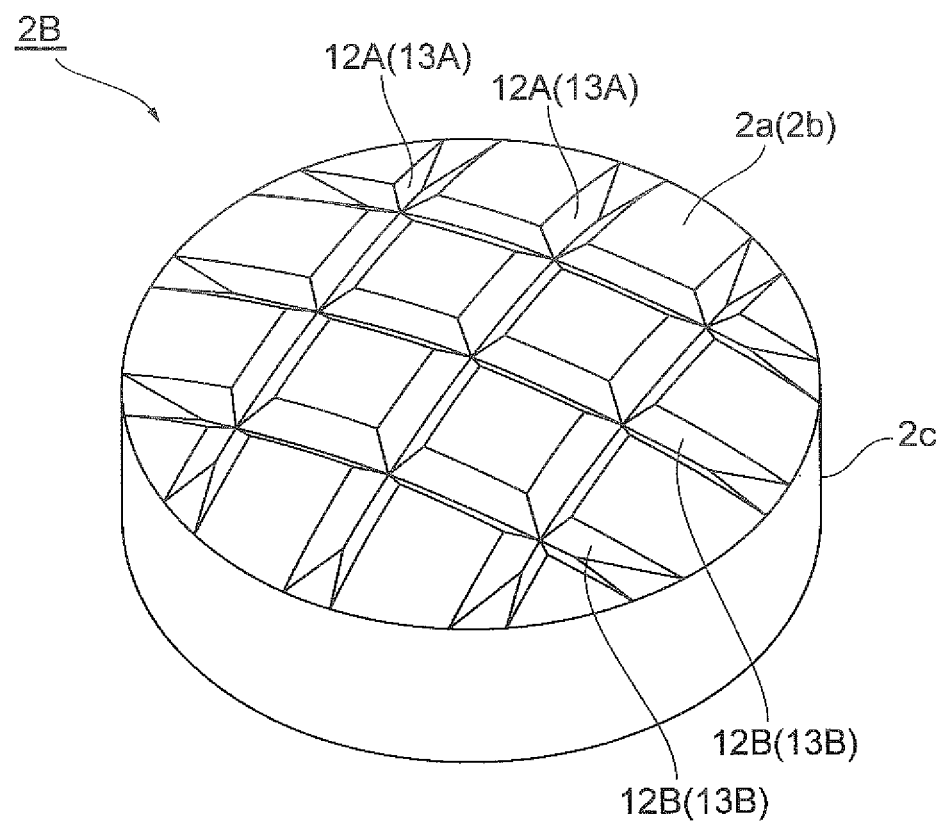
FIG. 7 is a perspective view showing another modified embodiment of the uncoated tablet of the inner core.
Figure 8:
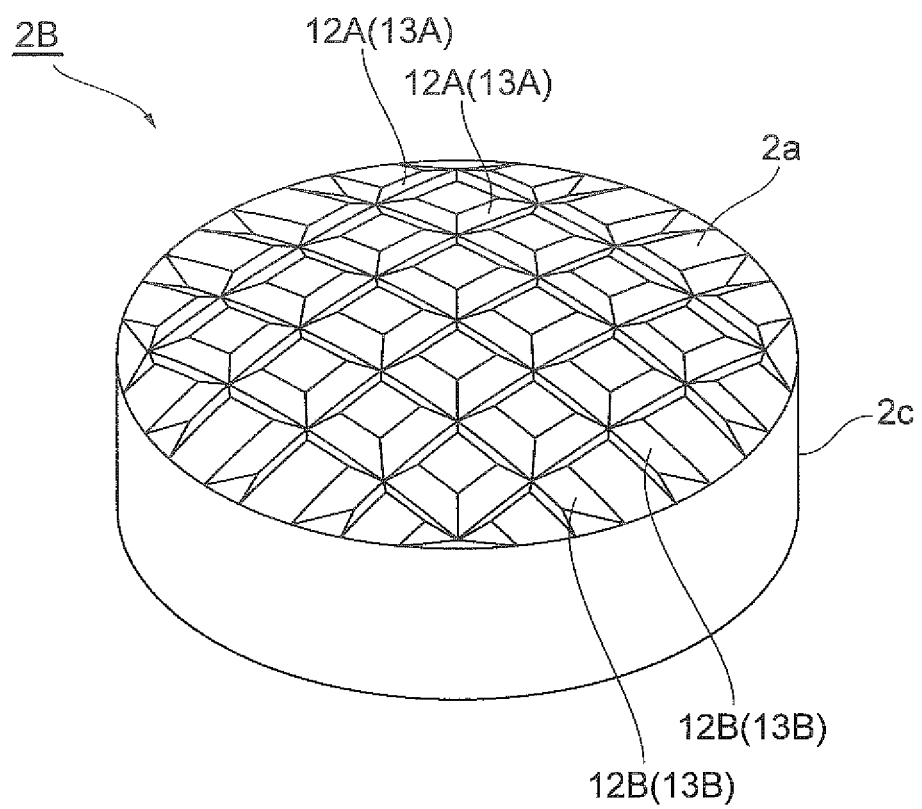
FIG. 8 is a perspective view showing another modified embodiment of the uncoated tablet of the inner core.

An inner core 2B shown in FIG. 7 is an inner core in the circular surface 2a of which a plurality of grooves 12A, 12A along mutually parallel lines and a plurality of grooves 12B, 12B along lines intersecting each groove 12A at right angles are provided in a grid and in the circular surfaces 2b of which similar grooves 13A, 13A and grooves 13A, 13A are provided in a grid. As shown in FIG. 8, the number of the grooves 12A and 12B and the grooves 13A and 13B may be further increased.

Figure 9:
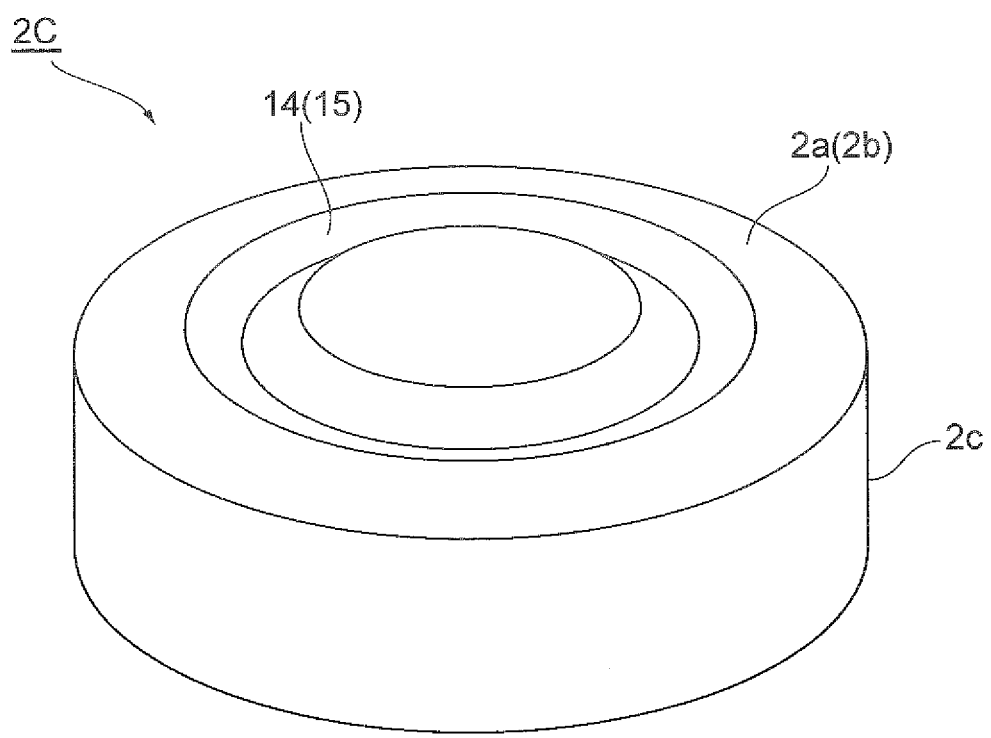
FIG. 9 is a perspective view showing another modified embodiment of the uncoated tablet of the inner core.

An inner core 2C shown in FIG. 9 is an inner core in circular surfaces 2a and 2b of which grooves 14 and 15 respectively are provided along a circular line along the circumferential edges. In this case, each radial direction of the inner core 2C and the grooves 14 and 15 intersect at the same angle. Thus, it is possible to obtain the effect to prevent misalignment of the inner core 2 and the outer layer 3 more uniformly in each radial direction of the inner core 2.

Figure 10:
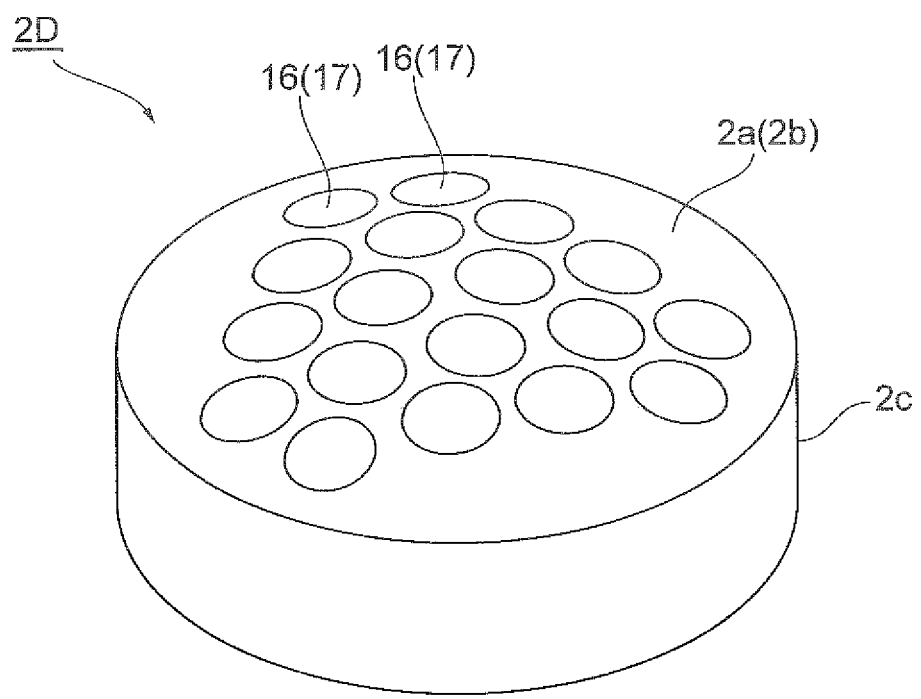
FIG. 10 is a perspective view showing another modified embodiment of the uncoated tablet of the inner core.

An inner core 2D shown in FIG. 10 is an inner core in a circular surface 2a of which a plurality of holes 16, 16 are provided to be interspersed and in a circular surfaces 2b of which similar holes 17, 17 are provided. Also with such hole-like recesses, the inner core 2D and the outer layer 3 are fitted to thereby become difficult to peel off from each other, while misalignment of the inner core 2D and the outer layer 3 is prevented.

Figure 11:
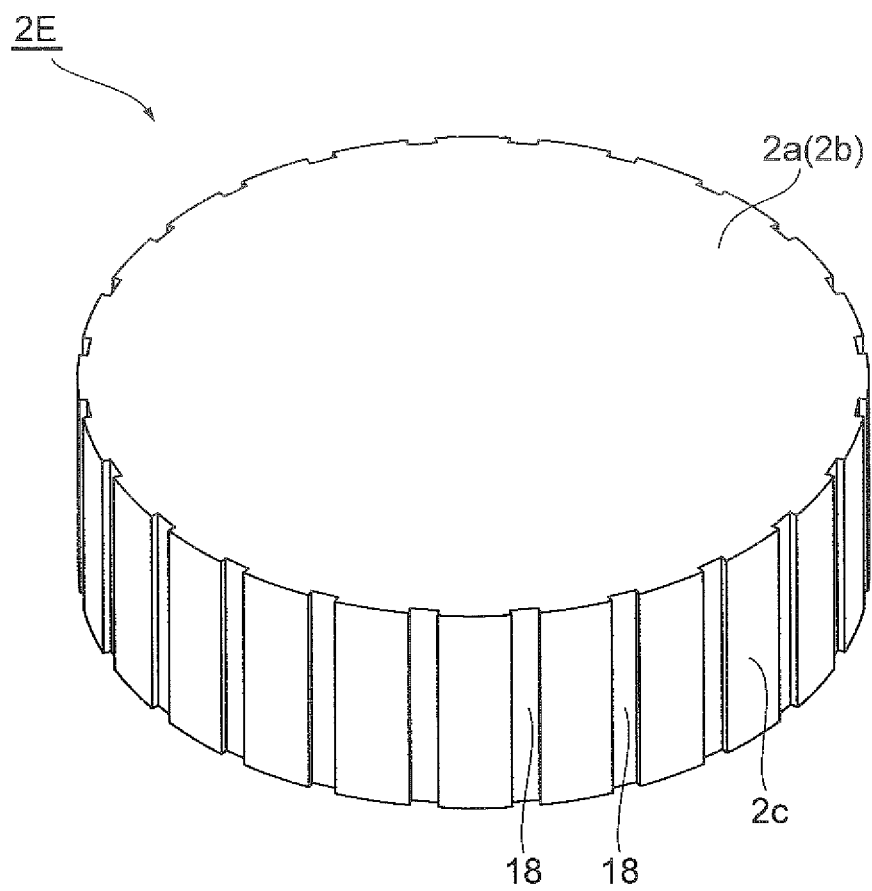
FIG. 11 is a perspective view showing another modified embodiment of the uncoated tablet of the inner core.

An inner core 2E shown in FIG. 11 is an inner core wherein a plurality of grooves 18, 18 are provided in a circumferential surface 2c instead of circular surfaces 2a and 2b. The grooves 18, 18 are arranged at substantially equal intervals along the circumferential direction of the inner core 2E. Each groove 18 is provided along the thickness direction of the inner core 2E, and both ends of each groove 18 are open to the circular surfaces 2a and 2b respectively. Each groove 18 may be inclined to the thickness direction of the inner core 2E. The strength of the dry-coated tablet 1 is enhanced also with such a groove 18. Additionally, since a plurality of grooves 18, 18 are arranged at substantially equal intervals along the circumferential direction of the inner core 2E, the strength of the dry-coated tablet 1 is further enhanced. Since each groove 18 is provided along the thickness direction of the inner core 2E, the circumferential direction of the inner core 2E intersects each groove 18. Thus, misalignment of the inner core 2E and the outer layer 3 is effectively prevented in the circumferential direction of the inner core 2E. Furthermore, since both ends of each groove 18 are open to the circular surfaces 2a and 2b respectively, the components in the outer layer 3 penetrate more smoothly into each groove 18 when dry-coated tableting of the outer layer 3 is carried out along the opposite direction of the circular surfaces 2a and 2b.

Figure 12:
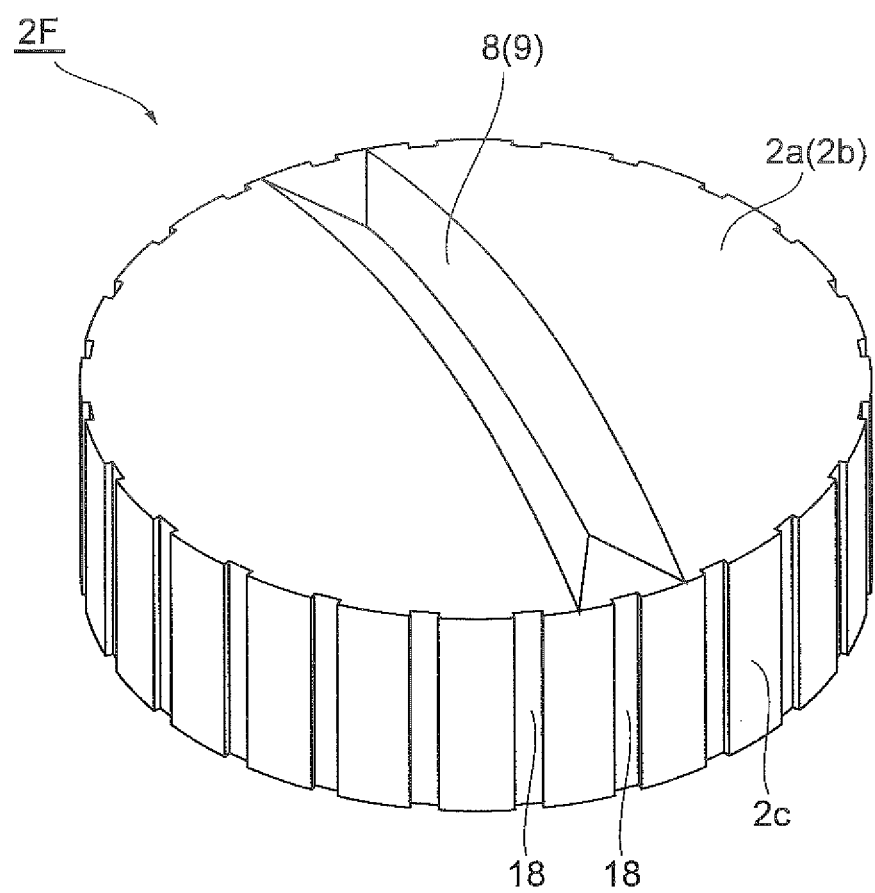
FIG. 12 is a perspective view showing another modified embodiment of the uncoated tablet of the inner core.

Recesses may be provided both in the circular surfaces 2a and 2b and the circumferential surface 2c. For example, as an inner core 2F shown in FIG. 12, grooves 8 and 9 are provided in circular surfaces 2a and 2b, while grooves 18, 18 may be provided in a circumferential surface 2c. Recesses to be formed in the circular surfaces 2a and 2b or the circumferential surface 2c may be characters, figures, and symbols formed as grooves.

In the inner cores 2A to 2F exemplified as above, the grooves 10A, 10B, 11A, 11B, 12A, 12B, 13A, 13B, 14, and 15 and holes 16 and 17 are formed by forming grooves or holes in the circular surfaces of an uncoated tablet with a tableting punch and applying a coating on the uncoated tablet. The groove 18 is formed by tableting an uncoated tablet using a tableting die having a groove in the inner surface of the hole in the die to form a groove in the circumferential surface of the uncoated tablet and applying a coating on this. It is preferable that the opening width of the grooves 10A, 10B, 11A, 11B, 12A, 12B, 13A, 13B, 14, 15, and 18 and holes 16 and 17 be larger than the average particle size of a component the average particle size of which is the largest of the powdery solid components contained in the outer layer 3. It is preferable that the depth of the grooves 10A, 10B, 11A, 11B, 12A, 12B, 13A, 13B, 14, 15, and 18 and holes 16 and 17 be larger than the average particle size of a component the average particle size of which is the smallest of the powdery solid components contained in the outer layer 3, and it is more preferable that the depth be larger than the average particle size of a component the average particle size of which is the largest of the powdery solid components contained in the outer layer 3.

It is not essential that the inner cores 2A to 2F have the coating layer 5. When the inner cores 2A to 2F do not have the coating layer 5, the conditions described above concerning the opening width and depth of the recesses are applied to the opening width and depth of the recesses in the uncoated tablet.

It is preferable that the friability of the inner core 2A to 2F be 1% or less, and it is preferable that the friability of the uncoated tablets of the inner core 2A to 2F be also 1% or less.

It should be noted that, in the inner core 2 and the inner cores 2A to 2F, the cross sectional shapes of the recesses, such as the grooves 8, 9, 10A, 10B, 11A, 11B, 12A, 12B, 13A, 13B, 14, 15, and 18 and holes 16 and 17 are not limited to V-shaped, and may be rectangular, for example. The inner surfaces of the recesses may be curved. It is not necessary that recesses be provided in both the circular surfaces 2a and 2b, and recesses may be provided in either one of the surfaces.

Methods for forming recesses in an inner core are not limited to methods using a punch and a die for tableting uncoated tablets. For example, after an uncoated tablet in which there is no recess is tableted, recesses may be formed by blasting the uncoated tablet with abrasives. After an uncoated tablet in which there is no recess is tableted, recesses may be formed by methods such as inscribing, or particles of which grain size is coarse may be attached on the outer side of a coating layer to thereby form recesses between the particles.

Second Embodiment

A dry-coated tablet 1A according to a second embodiment is different from the dry-coated tablet 1 according to the first embodiment in that openings are formed in the outer surface of the inner core with through-holes formed in the inner core, instead of with the recesses formed in the inner core.

Figure 13:
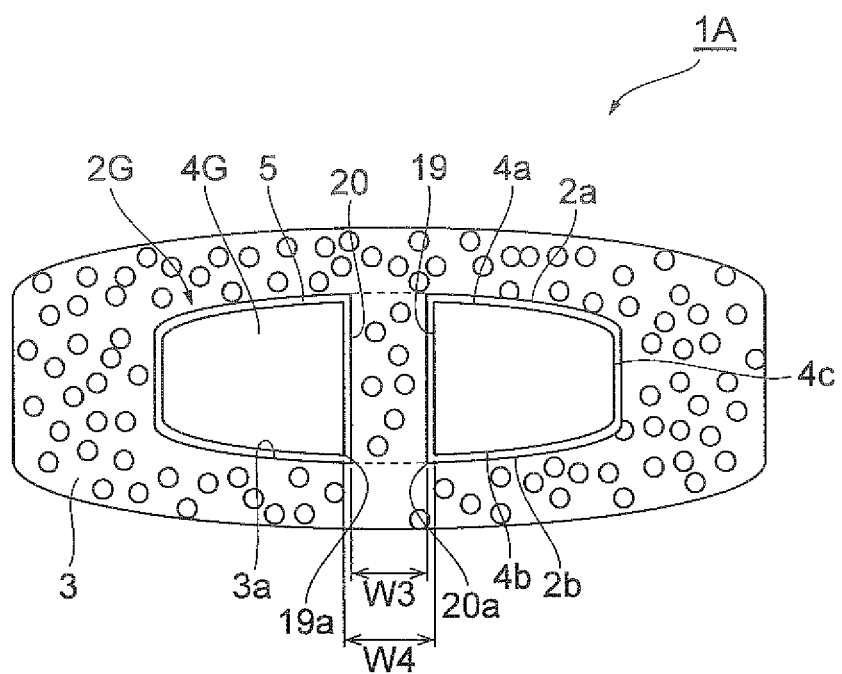
FIG. 13 is a schematic view showing a dry-coated tablet according to a second embodiment.

As shown in FIG. 13, an inner core 2G of the dry-coated tablet 1A has an uncoated tablet 4G and a coating layer 5. In the uncoated tablet 4G, a through-hole 19 is formed. The through-hole 19 is formed so as to connect circular surfaces 4a and 4b each other and is positioned in the center of the uncoated tablet 4G in planar view. An opening 19a is formed by the through-hole 19 each in the circular surfaces 4a and 4b. The through-hole 19 is formed with a tableting punch (mold) when the uncoated tablet 4G is tableted. The through-hole 19 may be formed by applying additional working such as drilling and punching after the uncoated tablet 4G is tableted.

The inner core 2G is composed by coating the outer surfaces of the uncoated tablet 4G with a coating layer 5. The coating layer 5 penetrates in the through-hole 19 in the uncoated tablet 4G, and thus, a through-hole 20 connecting circular surfaces 2a and 2b each other is formed also in the inner core 2G. An opening 20a is formed by the through-hole 20 in each of the circular surfaces (the outer surface of the inner core 2) 2a and 2b. The size of the opening 20a in the inner core 2G (the opening diameter) W3 is at least larger than the average particle size of a component the average particle size of which is the smallest of the powdery solid components contained in the outer layer 3. It is more preferable that the opening diameter W3 be larger than the average particle size of a component the average particle size of which is the largest of the powdery solid components contained in the outer layer 3.

It should be noted that it is not essential that the inner core 2G have the coating layer 5. When the inner core 2G does not have the coating layer 5, the conditions described above concerning the opening diameter 3 are applied to the opening diameter W4 of the through-hole 19.

In this way, it is possible to obtain the same effect as in the first embodiment also in the second embodiment in which the opening 20a is composed with the through-hole 20.

The through-hole 20 is formed so as to connect the circular surfaces 2a and 2b. As described above, dry-coated tableting of the outer layer 3 is carried out usually along the opposite direction of the circular surfaces 2a and 2b, that is, of the two surfaces opposed to each other so as to compress the components in the outer layer 3. Thus, if the through-hole 20 is formed so as to connect two surfaces opposed, the pressure of tableting becomes easy to act toward the inside of the through-hole 20, making it possible to allow the inner surface 3a of the outer layer 3 to penetrate into the opening 20c more securely.

It should be noted that the through-hole 20 may not be necessarily formed in the center in planar view and may be formed in a plurality of points in the inner core.

Although the suitable embodiments of the present invention have been described above, the present invention is not necessarily limited to the embodiments described above, and various variations can be made to the extent not departing from the spirit. The external shape of the inner core is not limited to the circular R-face shape described above. Each circular surface need not always be spherically expanded and may be planar. The inner core may form an elliptical shape and may form a triangular, quadrangular, pentagonal or more polygonal shape in planar view. It is not essential that the external shape of the inner core and the dry-coated tablet be a flat shape, the thickness of which is smaller than the diameter.

The outer layer may contain a PPI powder not forming fine granules such as enteric fine granules. Combinations of the active components contained in the inner core and the outer layer are not limited to the combination of acetylsalicylic acid and the PPI described above. For example, it is possible to apply the dry-coated tablet of the present invention to a combination of active components of which simultaneous ingestion is preferred, wherein separate preservation of the combination is preferred from the viewpoint of stability and the like. It is also possible to apply it to a combination in which the same active component is included in the inner core and the outer layer and each release rate is made different. Although it is not essential that both of the inner core and the outer layer contain the active components, it is preferable that at least one of the inner core and the outer layer contain the active components. An example of the inner core containing no active component includes those which serve as a core material for adjusting formulations. An example of the outer layer containing no active component include those which serve as a controlled-release layer which is mainly intended to control the release of the active components in the inner core.

Outside the coating layer of the inner core 2 and the inner cores 2A to 2G; a binding layer comprising components equivalent or more similar to the components in the outer layer 3 than the coating layers may be provided. That is, the inner core 2 and the inner cores 2A to 2G may further have a binding layer. Examples of the component equivalent or similar to the components in the outer layer 3 include excipients and binders, more specifically include lactose, white sugar, mannitol, xylitol, erythritol, starch, corn starch, crystalline cellulose, and light anhydrous silicic acid. When a binding layer is formed with excipients and binders, since the binding layer binds to the excipient and binders contained in the outer layer 3, the strength of the dry-coated tablets 1, and 1A is further enhanced. When a binding layer is formed with excipients and binders, the surface of the binding layer tends to be coarser than the surface of the coating layer. The strength of the dry-coated tablet 1 and 1A is also enhanced by this. By providing a binding layer, the inner core 2 or the inner cores 2A to 2G and the outer layer 3 become difficult to peel off from each other even at a position distant from the recesses in the inner core 2 or the inner cores 2A to 2G Thus, it is possible to further enhance the strength of the dry-coated tablets 1 and 1A.

Before dry-coated tableting is carried out, raw material powders or particles may be warmed to a temperature higher than room temperature. Dry-coated tableting carried out while warmed is referred to as "warm tableting" hereinafter. Temperature higher than room temperature is, for example from 30 to 50° C. Examples of the method for warming include methods for directly warming raw material powders or particles with non-contact type infrared heaters, warm-air or contact type resistance heaters and the like. Of tablet presses, areas which come in contact with raw material powders or particles may be warmed. Examples of the area which comes in contact with raw material powders or particles include punches, turn tables of rotary tablet presses, and rotary feeders. The entire tablet press may be warmed. Furthermore, gases with which a space where a tablet press is installed is filled may be warmed. When warm tableting is carried out in this way, it is possible to enhance the strength of the dry-coated tablet even without providing the inner core with recesses or through-holes. Thus, it is possible to further enhance the strength of the dry-coated tablet by combination of forming recesses or through-holes in the inner core and carrying out warm tableting.

EXAMPLES

Examples and Comparative Examples of the dry-coated tablet will be described hereinafter, but the present invention is not intended to be limited to these.

19

[Preparation of Tablets]

(1) Example 1

57000 g of acetylsalicylic acid (granulated product: Rhodine 3118 manufactured by Rhodia Co., Ltd.), 6270 g of corn starch, 3705 g of crystalline cellulose (CEOLUS PH-101 (trade name; manufactured by Asahi Kasei Corporation)), and 3705 g of carmellose were weighed and mixed in a tumbler mixer. This was tableted with a rotary tablet press (manufactured by KIKUSUI SEISAKUSHO LTD.) to obtain an uncoated tablet 4 having the grooves 6 and 7 described above. At this time, the grooves 6 and 7 were formed by carrying out tableting using a punch (mold) which has protrusions corresponding to the grooves 6 and 7. The diameter and weight of the uncoated tablet 4 were set to 7 mm and 124 mg. The opening width and depth of the grooves 6 and 7 were set to about 1 mm and about 0.3 mm.

Polysorbate 80 (4.8 g) was dissolved in 567.6 g of water and warmed to about 70° C., and 12.2 g of a glycerin monostearate was dispersed with a disperser to thereby obtain a glycerin monostearate dispersion. To this, 607.4 g (solids content 182.2 g) of methacrylic acid copolymer LD (Eudragit (Eudragit) L30D-55 (trade name; manufactured by Evonik Co., Ltd.)), 67.4 g (solids content 20.2 g) of methyl acrylate.methyl methacrylate copolymer (Eudragit NE30D (trade name; manufactured by Evonik Co., Ltd.)), 0.02 g of citric acid anhydride, and 40.4 g of triethyl citrate were added and mixed to thereby obtain an enteric coating liquid. A total of 620 g of a plurality of uncoated tablets 4 was simultaneously coated with this enteric coating liquid using a Dria Coater (manufactured by Powrex Co., Ltd.). Coating was carried out until 13 mg of the solid components in the enteric coating liquid was attached to the uncoated tablets 4 to thereby obtain inner cores 2 each of which is 137 mg. The opening width and depth of the grooves 8 and 9 in the inner core 2 were substantially equivalent to the opening width and depth of the grooves 6 and 7 before coating, and were about 1 mm and about 0.3 mm respectively.

Granulation was carried out by weighing 37800 g of lansoprazole enteric fine granules, 24080 g of D-mannitol, and 2660 g of crystalline cellulose and spraying 43400 g of a 6% hydroxypropyl cellulose solution with a fluidized bed granulator (Powrex Co., Ltd., FD-WS-60G) to thereby obtain outer layer granulated powder. In a tumbler mixer, 3750 g of crospovidone, 7850 g of crystalline cellulose (CEOLUS KG-1000 (trade name; manufactured by Asahi Kasei Corporation)), 2250 g of magnesium aluminometa silicate (Neusilin UFL2 (trade name; manufactured by Fuji Chemical Industry Co., Ltd.)), 1200 g of magnesium stearate, and 59950 g of the granulated powder described above were mixed to thereby obtain outer layer mixed powder.

The inner core 2 was coated with the outer layer mixed powder, and dry-coated tableting was carried out to thereby form the outer layer 3. The outer diameter of the outer layer 3 was set to 10 mm, and the total weight of the dry-coated tablet was set to 437 mg (the inner core 2: 137 mg, the outer layer 3: 300 mg). For dry-coated tableting, a rotary dry-coated tablet press (manufactured by KIKUSUI SEISAKUSHO LTD.) was used, the tableting pressure was set to 15 kN, and the rotating speed was set to 10 rpm. As described above, Example 1 of the dry-coated tablet was obtained. It should be noted that the average particle size of the component the average particle size of which was the smallest of the powdery solid components contained in the outer layer 3 was about 13 μm.

(2) Example 2

The shape of the punch for tableting the uncoated tablet 4 in Example 1 was changed to thereby obtain the inner core 2A having the cross-shaped grooves 10A, 10B, 11A, and 11B described above. The cross sectional shape of each groove was made a V-shape, the opening width was set to about 1 mm, and the depth was set to about 0.3 mm. The inner core 2A was used, and the enteric coating, the mixed powder of the outer layer 3 and other conditions were made the same as in Example 1 to thereby obtain Example 2 of the dry-coated tablet.

(3) Example 3

The shape of the punch for tableting the uncoated tablet 4 in Example 1 was changed to thereby obtain the inner core 2B having the grid-like grooves 12A, 12B, 13A, and 13B described above. The number of the grooves 12A, 12B, 13A, and 13B was each made three. The cross sectional shape of each groove was made a V-shape, the opening width was set to about 0.5 mm, and the depth was set to about 0.25 mm. The inner core 2B was used, and the enteric coating, the mixed powder of the outer layer 3 and other conditions were made the same as in Example 1 to thereby obtain Example 3 of the dry-coated tablet.

(4) Example 4

The shape of the punch for tableting the uncoated tablet 4 in Example 1 was changed to thereby obtain the inner core 2C having the round grooves 14 and 15 as described above. The diameter of a circle formed by the centerline of each grooves was set to about 4 mm. Additionally, the cross sectional shape of each groove was made a V-shape, the opening width was set to about 1 mm, and the depth was set to about 0.6 mm. The inner core 2C was used, and the enteric coating, the mixed powder of the outer layer 3 and other conditions were made the same as in Example 1 to thereby obtain Example 4 of the dry-coated tablet.

(5) Example 5

The shape of the punch for tableting the uncoated tablet 4 in Example 1 was changed to form an uncoated tablet in which there are no recesses. A hole was drilled in the uncoated tablet with a drill to thereby obtain the inner core 2G having the through-hole 20 described above. The inner diameter of the through-hole 20 (the opening diameter) was set to about 1 mm. The inner core 2G was used to thereby obtain Example 5 of the dry-coated tablet. For dry-coated tableting, Autograph was used, and the tableting pressure was set to 15 kN. The enteric coating, the mixed powder of the outer layer 3, and other conditions were made the same as in Example 1.

(6) Examples 6 to 10

The tableting pressure for dry-coated tableting each in Examples 1 to 5 was changed from 15 kN to 19 kN, and other conditions were made the same as in Examples 1 to 5 to thereby obtain Examples 6 to 10 of the dry-coated tablet.

(7) Reference Example 1

The shape of the punch for tableting the uncoated tablet 4 in Example 1 was changed to thereby obtain an inner core in which no recesses or through-hole was formed. The inner core was coated with an outer layer mixed powder which was similar to in Example 1, and warm tableting was carried out to thereby form the outer layer 3. The outer diameter of the outer layer 3 was set to 10 mm, and the total weight of the dry-coated tablet was set to 437 mg (the inner core: 137 mg, the outer layer: 300 mg). For warm tableting, AQUARIUS 3-K-DC (manufactured by KIKUSUI SEISAKUSHO LTD.) was used, and the turn table and the rotary feeder were warmed to about 40° C. The tableting pressure was set to 13 kN and the rotary speed was set to 25 rpm. Reference Example 1 of the dry-coated tablet was thereby obtained.

(8) Comparative Example 1

The shape of the punch for tableting the uncoated tablet 4 in Example 1 was changed to thereby obtain an inner core in which no recesses or through-hole was formed. The enteric coating, the mixed powder of the outer layer 3, and other conditions were made the same as in Example 1 to thereby obtain Comparative Example 1 of the dry-coated tablet.

(9) Comparative Example 2

The tableting pressure for dry-coated tableting in Comparative Example 1 was changed from 15 kN to 19 kN and other conditions were made the same as in Comparative Example 1 to thereby obtain Comparative Example 2 of the dry-coated tablet.

[Measurement of Friability]

Friability of the uncoated tablets of the inner core 2 and the inner cores 2A, 2B, and 2C used for the dry-coated tablets of Examples 1 to 4 was measured in accordance with the friability testing method in the Japanese Pharmacopoeia. The results of the measurements are shown in Table 1.

TABLE 1

| Type | Friability of the uncoated tablet of the inner core |
| --- | --- |
| Example 1 | 0.47% |
| Example 2 | 0.42% |
| Example 3 | 0.52% |
| Example 4 | 0.5% |

As shown in Table 1, the friability of the uncoated tablet of the inner core in any of Examples 1 to 4 was 1% or less.

[Measurement of Tablet Hardness]

Tablet hardness of dry-coated tablets of Examples 1 to 4, Examples 6 to 9, and Comparative Examples 1 and 2 was measured using a tablet continuous measuring instrument (JAPAN MACHINERY Co., Ltd., WHT-3MJ). Hardness of 10 tablets was measured for each Example. The averages of the results of the measurement for Examples 1 to 4 and Comparative Example 1 are shown in Table 2. The averages of the results of the measurement for Examples 6 to 9 and Comparative Example 2 are shown in Table 3.

TABLE 2

| Type | Hardness |
| --- | --- |
| Example 1 | 116N |
| Example 2 | 138N |
| Example 3 | 136N |

TABLE 2-continued

| Type | Hardness |
| --- | --- |
| Example 4 | 121N |
| Comparative Example 1 | 105N |

TABLE 3

| Type | Hardness |
| --- | --- |
| Example 6 | 148N |
| Example 7 | 153N |
| Example 8 | 158N |
| Example 9 | 143N |
| Comparative Example 2 | 132N |

As shown in Table 2, the tablet hardness in any of Examples 1 to 4 was higher than in Comparative Example 1. As shown in Table 2, the tablet hardness in any of Examples 6 to 9 was higher than in Comparative Example 2. From these results, it has been confirmed that the strength of the dry-coated tablet is enhanced by employing the inner cores 2, 2A, 2B, and 2C as described above. It should be noted that also in Examples 5 and 10, it was possible to produce dry-coated tablets without problems, as in Examples 1 to 4 and Examples 6 to 9. From the results of the measurements of the tablet hardness of Examples 1 to 4 and Examples 6 to 9, it is naturally assumed that the tablet hardness of Examples 5 and 10 is higher than in Comparative Examples 1 and 2.

INDUSTRIAL APPLICABILITY

The present invention can be used for tablets to supply active components in the body of a recipient.

REFERENCE SIGNS LIST

1 Dry-coated tablet
2, 2A, 2B, 2C, 2D, 2E, and 2F Inner core
2a and 2b Circular surfaces
2c Circumferential surface
3 Outer layer
3a Inner surface
4 Uncoated tablet
5 Coating layer
8, 9, 10A, 10B, 11A, 11B, 12A, 12B, 13A, 13B, 14, 15, and 18 Grooves (Recesses)
16 and 17 Holes (Recesses)

The invention claimed is:
1. A dry-coated tablet comprising:
an inner core comprising a first active component; and
an outer layer comprising a plurality of powdery solid components and a second active component, wherein the outer layer coats the inner core, and wherein each of the powdery solid components is a group of particles having the same chemical composition;
wherein an opening is formed in an outer surface of the inner core, the opening is larger than an average particle size of the one of the plurality of powdery solid components having the smallest average particle size contained in the outer layer, and an inner surface of the outer layer penetrates in the opening,
wherein the inner core comprises an uncoated tablet and a coating layer coating the uncoated tablet, wherein a recess corresponding to the opening is formed in the uncoated tablet and the coating layer coats the uncoated tablet in the recess, and wherein a depth of the recess is larger than the average particle size of the one of the components.

2. The dry-coated tablet according to claim 1, wherein the recess is formed as a groove.

3. The dry-coated tablet according to claim 1, wherein the recess is formed as a hole interspersed in the outer surface of the inner core.

4. The dry-coated tablet according to claim 1, wherein the inner core has two surfaces arranged opposed to each other, and the recess is formed in at least one of the two surfaces.

5. The dry-coated tablet according to claim 1, wherein the inner core has two surfaces arranged opposed to each other and a circumferential surface arranged between circumferential edges of the two surfaces, and the recess is formed in the circumferential surfaces.

6. A dry-coated tablet comprising:

an inner core comprising a first active component; and an outer layer comprising a plurality of powdery solid components and a second active component, wherein the outer layer coats the inner core, and wherein each of the powdery solid components is a group of particles having the same chemical composition;

wherein an opening is formed in an outer surface of the inner core, the opening is larger than an average particle size of the one of the plurality of powdery solid components having the smallest average particle size contained in the outer layer, and an inner surface of the outer layer penetrates in the opening, wherein the inner core comprises an uncoated tablet and a coating layer coating the uncoated tablet, and wherein a through-hole corresponding to the opening is formed in the uncoated tablet and the coating layer coats the uncoated tablet in the through-hole.

7. The dry-coated tablet according to claim 6, wherein the inner core has two surfaces arranged opposed to each other, and the through-hole is formed so as to connect the two surfaces.

8. The dry-coated tablet according to claim 1, wherein the first and second active components are the same as or different from one another.

9. The dry-coated tablet according to claim 1, wherein the second active component contained in the outer layer forms a granule together with components other than the second active component.

10. The dry-coated tablet according to claim 1, wherein a friability of the inner core is 1% or less.

11. The dry-coated tablet according to claim 1, wherein the friability of the uncoated tablet is 1% or less.

12. The dry-coated tablet according to claim 1, wherein a width of the recess is greater than or equal to 0.5 mm and the depth of the recess is greater than or equal to 0.25 mm.

* * * * *

UNITED STATES PATENT AND TRADEMARK OFFICE
CERTIFICATE OF CORRECTION

PATENT NO. : 9,693,962 B2
APPLICATION NO. : 14/405310
DATED : July 4, 2017
INVENTOR(S) : Kawano It is certified that error appears in the above-identified patent and that said Letters Patent is hereby corrected as shown below:

On the Title Page

Item (73): After "Assignee:", delete "Takeda Pharmaceutical Limited," and insert --Takeda Pharmaceutical Company Limited,--.

Signed and Sealed this
Fifth Day of September, 2017

Joseph Matal
*Performing the Functions and Duties of the*
*Under Secretary of Commerce for Intellectual Property and*
*Director of the United States Patent and Trademark Office*